United States Patent [19]

Dixon et al.

[11] Patent Number: 5,109,016
[45] Date of Patent: Apr. 28, 1992

[54] METHOD FOR INHIBITING INFECTION OR REPLICATION OF HUMAN IMMUNODEFICIENCY VIRUS WITH PORPHYRIN AND PHTHALOCYANINE ANTIVIRAL COMPOSITIONS

[75] Inventors: Dabney W. Dixon, Atlanta; Raymond F. Schinazi, Decatur; Luigi G. Marzilli, Atlanta, all of Ga.

[73] Assignees: Georgia State University Foundation, Inc.; Emory University, both of Atlanta, Ga.

[21] Appl. No.: 355,499

[22] Filed: May 22, 1989

Related U.S. Application Data

[63] Continuation-in-part of Ser. No. 197,764, May 23, 1988.

[51] Int. Cl.⁵ ............................................. A61K 31/40
[52] U.S. Cl. .................................... 514/410; 514/185; 540/145; 530/826
[58] Field of Search ............... 540/145; 514/185, 410; 530/826

[56] References Cited

U.S. PATENT DOCUMENTS

| | | | |
|---|---|---|---|
| 4,522,811 | 6/1985 | Eppstein et al. | 514/2 |
| 4,614,723 | 9/1986 | Schmidt et al. | 540/145 X |
| 4,649,151 | 3/1987 | Dougherty et al. | 540/145 X |
| 4,675,338 | 6/1987 | Bommer et al. | 540/145 X |
| 4,878,891 | 11/1989 | Judy et al. | 424/101 |

FOREIGN PATENT DOCUMENTS

86106646.2  5/1986  European Pat. Off. .
196515  10/1986  European Pat. Off. .

OTHER PUBLICATIONS

Adler, A. D., Longo, F. R., Finarelli, J. D., Goldmacher, J., Assour, J., and Korsakoff, L., *J. Org. Chem.*, 32, 476 (1967).
Adler, A. D., Longo, F. R., and Varadi, V., *Inorg. Syn.*, 16, 213–220 (1976).
Bhat and Padmanaban, *Biochemical and Biophysical Research Communications* 151 (2) 737 (1988).
Bhattacharya, P., *Proc. Natl. Acad. Sci. U.S.A.*, 78 (5), 2683 (1981).
Cozzani et al., *Chem. Biol. Interact.*, 53 131 (1985).
Dwarki, V., et al., *J. Biol. Chem.*, 262 (35), 16958 (1987).
Gonzales and Weedon, *Canadian Journal of Chemistry* 63 (3), 602 (1985).
Jori, G., *Br. J. Cancer*, 53 (5), 615 (1986).
Jori, G. et al., *Br. J. Cancer*, 48, 307 (1983).
Kappas and Drummond, *J. Clin. Invest.*, 77, 335 (1986).
Lavallee, D. K., *Coments Inorg. Chem.*, 5, 155–174 (1986).
Lewin et al., *Proceedings of the Society for Experimental Biology and Medicine*, 163 81 (1980).
Lindsey et al., *J. Org. Chem.*, 52, 827–836 (1987).
Momenteau, M., Loock, B., Huel, C. and Lhoste, J. M., *J. Chem. Soc.*, Perkin Trans. 1 283 (1988).
Morgan, B. and Dolphin, D., *J. Org. Chem.* 52, 5364–5374 (1987).
Munson, *Research Communications and Chemical pathology and Pharmacology* 16 (1), 175 (1977).
Oseroff et al., *Proc. Natl. Acad. Sci. U.S.A.* 83, 8744 (1986).
Perlin et al., *Ant-viral Research* 7, 43 (1987).
Schnipper et al., *J. Clin. Invest.* 65, 432 (1980).
Sicuro et al., *Med. Biol. Environ.* 16, 67 (1987).
Smith, K. M. and Minnetian, O. M., *J. Chem. Soc., Perkin Trans. 1* 277–280 (1986).
Smith, K. M., Parish, D. W. and Inouye, W. S., *J. Org. Chem.* 51, 666–671 (1987).

(List continued on next page.)

Primary Examiner—Richard L. Raymond
Attorney, Agent, or Firm—Kilpatrick & Cody

[57] ABSTRACT

Compositions for the inhibition of replication of human immunodeficiency virus containing one or more "porphyrins" possessing antiviral activity. As used herein "porphyrins" includes porphyrins, phthalocyanines, chlorins, metallo derivatives thereof, and other porphyrin-like compounds. Examples of natural and synthetic, positively, negatively, and neutrally charged porphyrins, phthalocyanines, and derivatives thereof have been found to exhibit selective anti-HIV activity which is not dependent on the presence of light.

13 Claims, 2 Drawing Sheets

OTHER PUBLICATIONS

Tsutsui and Mueller, *Biochemical and Bioresearch Communications* 149 (2) 628 (1987).
Yoshida et al., *Eur. J. Biochem.* 171, 457 (1988).
Leznoff et al., *Photochem. Photobiol.* 49(3), 279–284 (1989).
Ben-Hur, et al., *Photochem. Photobiol.* 46(5), 651–656 (1987).
Sonoda et al., *Photochem. Photobiol.* 46(5), 625,631 (1987).
Tralau et al., *Photochem. Photobiol.* 49(3), 305–312 (1989).
Langlois et al., *Photochem. Photobiol.* 44(2), 117–123 (1986).
Lier et al., *Photosensitisation* Ed. G. Moreno, et al. (Springer-Verlag, Berlin 1988).
Biolo and Menegaldo, *Photosensitisation* Ed. G. Moreno et al., (Springer-Verlag, Berlin 1988).
Ben-Hur et al., *Photomedicine* vol. III, Eds. Ben-Hur and Rosenthal (CRC Press, Inc., Boca Raton, Fla.).
Spikes, *Photochem. Photobiol.* 43(6), 691–699 (1986).
Kreimer-Birnbaum, "Modified Porphyrins, Chlorins, Phthalocyanines, and Purpurins: Second-Generation Photosensitizers for Photodynamic Therapy", pp. 157–173.
Brasseur et al., *Photochem. Photobiol.* 42(5), 515–521 (1985).
Brasseur et al., *Photochem. Photobiol.* 47(5), 705–711 (1988).
Brasseur et al., *Photochem. Photobiol.* 46(5), 739–744 (1987).
Chan et al., *Cancer Letters* 44, 73–77 (1989).
Ben-Hur et al., *Int. J. Radiat. Biol.* 51(3), 467–476 (1987).
Berg et al., *Cancer Letters* 44, 7–15 (1989).
Hunting et al., *Photochem. Photobiol.* 45(6), 769–773 (1987).
Ramakrishnan et al., *Photochem. Photobiol.* 48(3), 297–303 (1988).
Firey et al., *Photochem. Photobiol.* 48(3), 357–360 (1988).
Paquette et al., *Photochem. Photobiol.* 47(2), 215–220 (1988).
Milanese et al., *Photochem. Photobiol.* 46(5), 675–681 (1987).
Singer et al., *Photochem. Photobiol.* 46(5), 745–749 (1987).
Chan et al., *Photochem. Photobiol.* 46(5), 867–871 (1987).
Archotolarygol Head Neck Surg., vol. 112:42–46, 1986, "Hematoporphyrin Derivative Therapy", Shikowitz et al.
Journal of Investigative Dermatology, 80:0665–0745, 1983, "The Nature and Molecular Basis of Cutaneous Photosensitivity Reactions to Psoralens and Coal Tar", Pathak et al.

METHOD FOR INHIBITING INFECTION OR REPLICATION OF HUMAN IMMUNODEFICIENCY VIRUS WITH PORPHYRIN AND PHTHALOCYANINE ANTIVIRAL COMPOSITIONS

This is a continuation-in-part of U.S. Ser. No. 197,764 entitled "Porphyrin Antiviral Compositions" filed May 23, 1988 by Dabney W. Dixon, Raymond F. Schinazi, and Luigi G. Marzilli.

BACKGROUND OF THE INVENTION

This application relates to the field of antiviral compounds, specifically porphyrin and porphyrin-like compounds, such as phthalocyanines and chlorins, for the inhibition of infection and replication of human immunodeficiency virus.

AIDS, or acquired immunodeficiency disease, is characterized by an imbalance in two basic types of immune system cells, helper/inducer T lymphocytes and suppressor T lymphocytes, with the ratio of suppressor cells to helper/inducer cells greatly elevated. Helper/inducer T cells, defined by a surface antigen called CD4, are responsible for the induction of most of the functions of the human immune system, including the humoral immune response involving the production of antibodies by B lymphocytes and the cell-mediated response involving stimulation of cytotoxic T cells. A condition associated with HIV is AIDS-related complex, or ARC. Most patients suffering from ARC eventually develop AIDS.

Two related retroviruses can cause AIDS, human immunodeficiency virus type 1 and type 2 (HIV-1 and HIV-2, generally referred to herein as HIV). The genomes of the two viruses are about 50% homologous at the nucleotide level, contain the same complement of genes, and appear to attack and kill the same human cells by the same mechanism. Also known as LAV (lymphadenopathy-associated virus), HTLV-3 (human T-lymphotropic virus-type 3), and ARV (AIDS-related virus), HIV-1 was identified in 1983. Virtually all AIDS cases in the U.S. are associated with HIV-1 infection. HIV-2 was isolated in 1986 from West African AIDS patients.

Both types of HIV are retroviruses, in which the genetic material is RNA rather than DNA. The viruses carry with them a polymerase (reverse transcriptase) that catalyzes transcription of viral RNA into double-helical DNA. The viral DNA can exist as an unintegrated form in the infected cell or be integrated into the genome of the host cell. As presently understood, the HIV enters the T4 lymphocyte where it loses its outer envelope, releasing viral RNA and reverse transcriptase. The reverse transcriptase catalyzes synthesis of a complementary DNA strand from the viral RNA template. The DNA helix then inserts into the host genome where it is known as the provirus. The integrated DNA may persist as a latent infection characterized by little or no production of virus or helper/inducer cell death for an indefinite period of time. When the viral DNA is transcribed and translated by the infected lymphocyte, new viral RNA and proteins are produced to form new viruses that bud from the cell membrane and infect other cells.

No treatment capable of preventing or reversing the immunodeficiency of AIDS or ARC is currently available. All patients with opportunistic infections and approximately half of all patients with Kaposi's sarcoma have died within two years of diagnosis. Attempts at reviving the immune systems in patients with AIDS have been unsuccessful.

A number of compounds have apparent antiviral activity against this virus, including HPA-23, interferons, ribavirin, phosphonoformate, ansamycin, suramin, imuthiol, penicillamine, carbovir, 3'-azido-3'-deoxythymidine (AZT), and other 2',3'-dideoxy-nucleosides, such as 2',3'-dideoxycytidine (DDC), 2',3'-dideoxyadenosine (DDA), 2',3'-dideoxyinosine (DDI), 3'-azido-2',3'-dideoxyuridine (AzddU), 2',3'-dideoxy-2',3'-didehydrocytidine (D4C), 3'-deoxy-2',3'-didehydrothymidine (D4T) and 3'-azido-5-ethyl-2',3'-dideoxyuridine (AedU).

Inhibitors of cellular processes will often limit viral replication. Unfortunately, they are also usually toxic for the host and therefore cannot be prescribed for a prolonged period of time because of their toxicity. Although AZT is the drug of choice at this time for the treatment of AIDS, preliminary results indicate that AZT exhibits toxicity in a clinical setting, causing bone marrow suppression, resulting in anemia and neutropenia. See Yarchoan et al., *Lancet* 575-580 (1986).

Efforts to decrease the problem of toxicity have primarily been directed towards finding selective, less toxic drugs. Due to the exorbitant cost of the nucleoside type drugs, research has also been directed towards compounds which are relatively easy and economical to manufacture.

Photodynamic therapy (PDT) is the treatment of malignant tumors with photosensitizers, such as porphyrins and phthalocyanines. Briefly, certain photosensitizers, including porphyrins, metalloporphyrins, and phthalocyanines, localize preferentially in tumor cells. Irradiation of the tissue results in selective cell death of the cells carrying the photosensitizer. Red light in the therapeutically useful range of 600-1200 nm is used. Light in this region of the spectrum has increased transmittance in biological tissue. Both porphyrins and the structurally similar phthalocyanines absorb red light. While porphyrins have been studied more extensively, phthalocyanines have improved absorbance properties and higher extinction coefficients in this region of the spectrum.

General reviews of photodynamic therapy are by Gomer, C. J., et al., "Proceedings of the Clayton Foundation Conference on Photodynamic Therapy." *Photochem. Photobiol.* 46, 561-952 (1987) and Dougherty, T. J., *Photochem. Photobiol.* 45, 879-889 (1987).

The photochemistry and photophysics of porphyrins, metalloporphyrins, and phthalocyanines have been studied in detail. Processes observed include radiationless decay to ground, loss of an axial ligand, energy transfer, electron transfer, formation of singlet oxygen, phosphorescence and fluorescence. The photoprocesses observed in each system depend greatly on the central ligand, normally a metal (2H for porphyrin), the oxidation state of the metal and the axial ligand bound to the metal. A weaker dependence of the photophysical properties on the nature of the macrocycle is observed.

Porphyrins and phthalocyanines have been reported to have a variety of other biological activities. However, relatively little has been done with them with respect to in vivo clinical applications other than in photodynamic tumor therapy.

Perlin, et al., *Antiviral Res.* 7, 43-51 (1987), recently reported that, upon exposure to light, hematoporphyrin, at concentrations as low as 0.5 µg/ml, inhibits in vitro replication of influenza A and herpes simplex viruses, but not several other viruses. See also Lewin, et al., *Proc. Soc. Exper. Biol. Med.* 163, 81-90 (1980) and Schnipper, et al., *J. Clin. Invest.* 65, 432-438 (1980). Hematoporphyrin in combination with visible light also inhibits reverse transcription in vitro by the RNA-dependent DNA polymerase of Moloney leukemia virus from an exogenous template, as described by Munson, et al., *Res. Commun. Chem. Pathol. Pharmacol.* 16,175-178 (1977). Inhibition does not occur in the absence of exposure of the cells or viruses to light.

Within the last few months, hemin, ferric chloride protoporphyrin IX, has been shown to exhibit selective antiviral activity under certain conditions. Tsutsui and Mueller demonstrated in *Biochem.Biophys.Res.Com.* 149(2),628-634 (December 1987) that the reverse transcriptase activity of Rauscher murine leukemia virus, but not of avian myeloblastosis virus, was inhibited by hemin at a concentration of $10^{-4}$ M. They proposed that the hemin inhibited the reverse transcriptase activity by reversible, non-covalent interaction with the enzyme, not the RNA template.

Bhattacharya, et al., *Proc. Natl. Acad. Sci. USA* 78(5),2683-2687 (1981) showed that hemin differentially inhibits three forms of DNA polymerase α, supporting the theory that hemin may be an important modulatory protein. None of these researchers correlated inhibition with toxicity, however, nor examined the compounds as selective antiviral drugs.

Ben-Hur, et al., *Photochem. and Photobiol.*, 46(5):651-656, (1987) demonstrated that the incorporation of thymidine, uridine, and leucine, into DNA, RNA, and protein respectively, is inhibited in log-phase Chinese hamster cells that are photosensitized with chloroaluminium phthalocyanine tetrasulfonate. There are no known reports demonstrating that phthalocyanines possess antiviral activity.

It is therefore an object of the present invention to provide compounds having selective activity against Human Immunodeficiency Virus.

It is a further object of the present invention to provide compounds having antiviral activity which are relatively non-toxic.

It is a still further object of the present invention to provide compounds having antiviral activity which are relatively inexpensive and easy to manufacture.

SUMMARY OF THE INVENTION

Compositions for the inhibition of replication of Human Immunodeficiency Virus containing one or more porphyrin or porphyrin-like compounds, including phthalocyanines, chlorins, and metallo derivatives thereof, and methods for use thereof both in vitro and in vivo.

Porphyrins and porphyrin-like compounds, such as phthalocyanines, are tetrapyrrole macrocycle compounds with bridges of one carbon or one nitrogen joining the pyrroles. The term porphyrin is used herein to mean porphyrins, phthalocyanines, chlorins, metallo derivatives thereof and other porphyrin-like compounds unless otherwise stated.

Many porphyrins are isolated from nature, for example, protoporphyrin, while many other porphyrins and phthalocyanines are made synthetically. Derivatives of porphyrins and phthalocyanines include compounds with one or more substituents on one or more of the rings, compounds in which the conjugation of the ring has been altered by addition of substituents, and compounds in which one or more center nitrogens is attached to substituents such as metals, liganded metals, and organic moieties.

Phthalocyanines are porphyrin-like synthetic compounds that are structurally and functionally related to porphyrins. The phthalocyanine ring system is similar to that of the porphyrin ring system with the addition of an aromatic ring on each pyrrole ring and the replacement of the meso position carbon atoms by nitrogen atoms.

Examples of natural and synthetic, positively charged, negatively charged, and neutrally charged porphyrins and porphyrin derivatives and phthalocyanines have been found to exhibit selective anti-HIV activity. The activity is not dependent on the presence of light. The compounds did not inhibit replication of herpes simplex type 1 or type 2 or Coxsackievirus strain B4. Effective concentrations for inhibition of HIV-1, as measured in vitro by inhibition of replication, range from 0.01 to greater than 100 µM. Compounds which are useful are those having a therapeutic index of greater than 10, toxicity at levels of greater than or equal to 100 µM, and antiviral activity at concentrations of less than equal to 10 µM. Most of the compounds were not toxic to uninfected PBM cells at levels of less than 100 µM.

DETAILED DESCRIPTION OF THE INVENTION

Figure 1A:
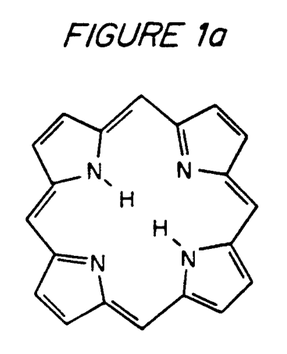
FIG. 1A is the porphyrin ring system.

Porphyrins are macrocycle compounds with bridges of one carbon atom or one nitrogen atom respectively, joining the pyrroles to form the characteristic tetrapyrrole ring structure. There are many different classes of porphyrin-like compounds. The term porphyrins will be used herein to refer to porphyrins (FIG. 1A), phthalocyanines, chlorins, metallo derivatives thereof, and other porphyrin-like compounds possessing antiviral activity.

Figure 1B:
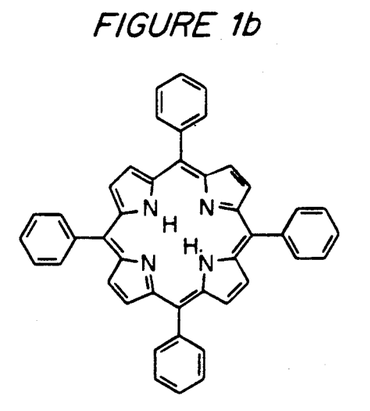
FIG. 1B is tetraphenylporphyrin.

Some porphyrins are isolated from nature, for example, protoporphyrin IX, which is the organic portion of hemin. Many derivatives of natural porphyrins are known (see, for example Smith and Cavaleiro, "Protoporphyrin-IX: Some Useful Substituent Manipulations", *Heterocycles*, 26,1947-1963, (1986)). Many other porphyrins and phthalocyanines are synthesized in the laboratory. These include those made via the condensation of aldehydes and pyrroles, such as tetraphenylporphyrin (FIG. 1B). They also include compounds built up from smaller organic fragments.

Porphyrin-like compounds can have one or more substituents, and combinations of one or more different substituents. The substituents can be symmetrically or unsymmetrically located. The substituents, as well as the overall structure, can be neutral, positively charged or negatively charged. Charged structures have counterions, and many counterions and combinations of counterions are possible.

Porphyrins can be covalently attached to other molecules, for example, cyclodextrins (Gonzalez, M. C.; Weedon, A. C. *Can. J. Chem.* 63, 602–608 (1985)). They can have an attached molecular superstructure. The conjugation of the ring can be altered by addition of one or more substituents. In addition, metals can be inserted into the tetrapyrrole ring. Examples of such metals include, but are not limited to, Fe, Co, Zn, Mo, Ti, Mn, Cr, Ni, Mg, Cu, Tl, In, Ru, V and Au. Additional ligands can be attached to the metal.

As reported in U.S. Serial No. 197,764 entitled "Porphyrin Antiviral Compositions" filed May 23, 1988 by Dabney W. Dixon, Raymond F. Schinazi, and Luigi G. Marzilli, a variety of porphyrins have been found to have selective activity against HIV-1 when tested in cell culture. As reported herein, phthalocyanines have now been demonstrated to have selective activity against HIV-1 when tested in cell culture.

Figures 2A, 2B:
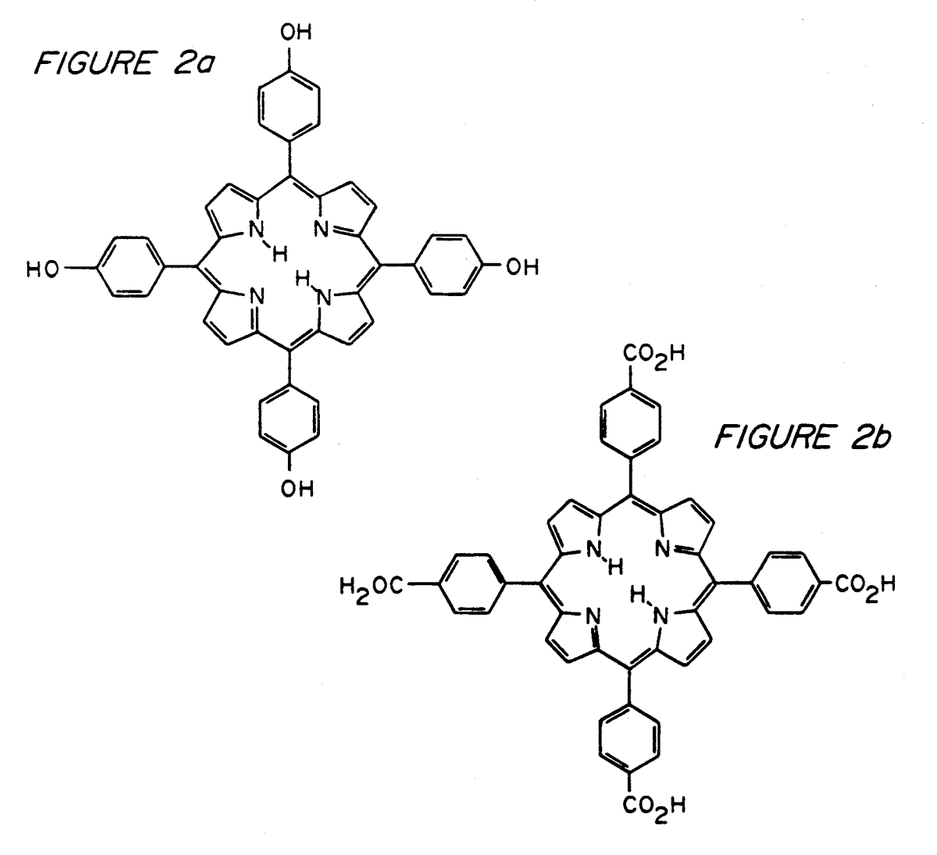
FIG. 2A is a derivative of tetraphenylporphyrin, tetra-(4-hydroxyphenyl)porphyrin.
FIG. 2B is a derivative of tetraphenylporphyrin, tetra-(4-carboxyphenyl)porphyrin.
Figures 3A, 3B, 4, 5:
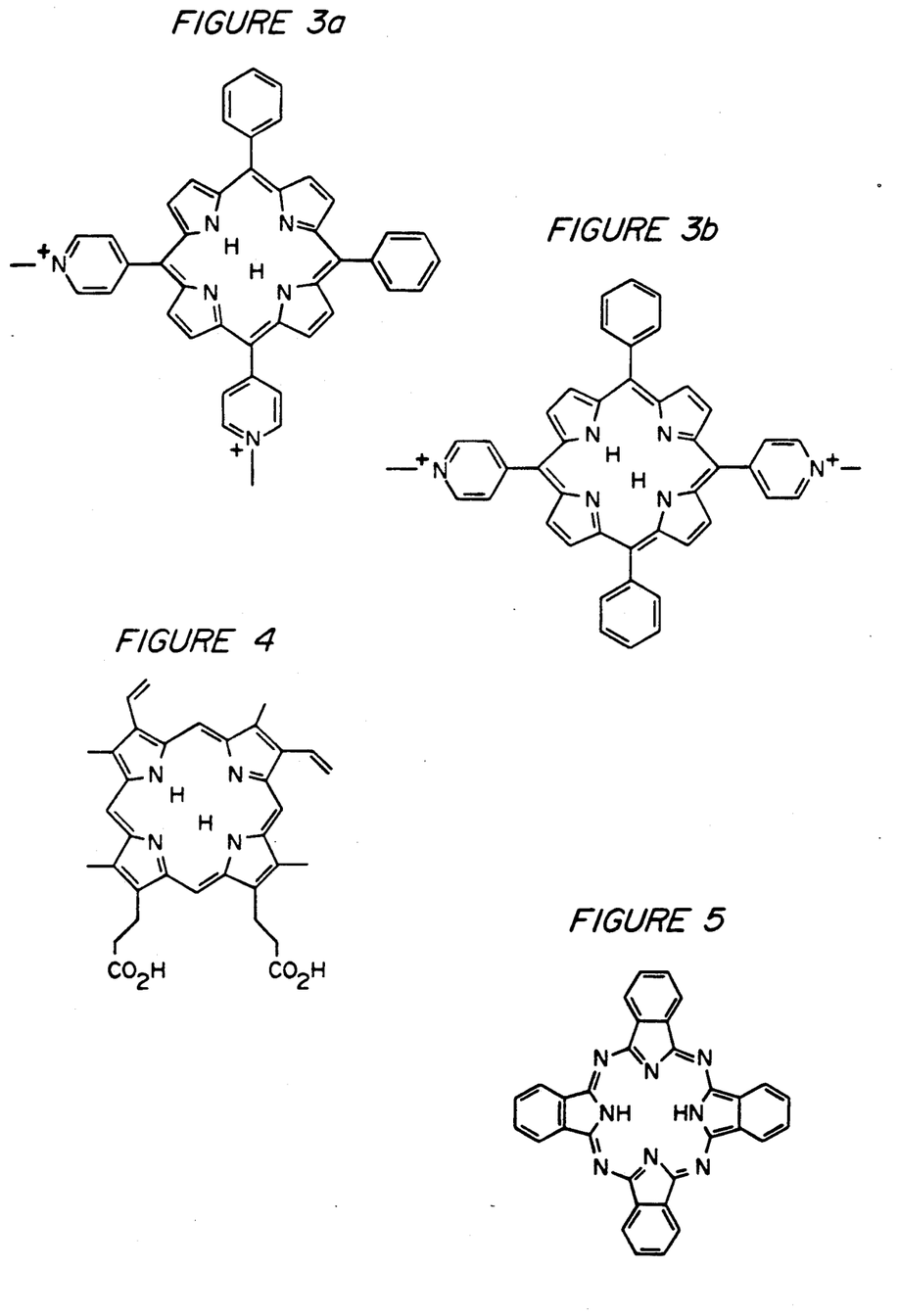
FIG. 3A is 5,10-Diphenyl-15,20-di(N-methyl-4-pyridyl)-porphyrin.
FIG. 3B is 5,15-Diphenyl-10,20-di(N-methyl-4-pyridyl)-porphyrin.
FIG. 4 is protoporphyrin free acid.
FIG. 5 is the phthalocyanine ring structure.

Both natural and synthetic porphyrins, phthalocyanines and metallo derivatives thereof were tested for inhibition of reverse transcriptase. Compounds tested included 5,10-Diphenyl-15,20-di(N-methyl-3-pyridyl)-porphyrin; 5,10-Diphenyl-15,20-di(N-methyl-4-pyridyl)-porphyrin (FIG. 3A); 5,15-Diphenyl-10,20-di(N-methyl-3-pyridyl)-porphyrin (FIG. 3B); Hemin; Protoporphyrin (FIG. 4); Tetra-(N-methyl-4-pyridyl)-porphyrin; Mesotetraphenylporphine; Protoporphyrin IX dimethyl ester; Tetra-(4-carboxyphenyl)-porphyrin (FIG. 2B); Tetra(4-methylphenyl)-porphyrin; Tetra-(3-methylphenyl)porphyrin; Tetra-(4-hydroxyphenyl)-porphyrin (FIG. 2A); Fe(III)-tetraphenyl-porphyrin; Tetra-(4-chlorophenyl)-porphyrin; Fe(III)-tetra-(4-methylphenyl)-porphyrin; Fe(III)-tetra-(N-methyl-4-pyridyl)-porphyrin; Fe(III)-mu-oxo-dimer of tetraphenylporphyrin; copper phthalocyanine tetrasulfonic acid tetrasodium salt; nickel phthalocyanine tetrasulfonic acid; copper phthalocyanine 3,4',4'',4'''-tetrasulfonic acid; copper phthalocyanine; copper-4,4',4'',4'''-tetraaza29H, 31H-phthalocyanine (FIG. 5); cobalt phthalocyanine; reactive blue 15; and silicon phthalocyanine dichloride.

Protohemin was obtained from Aldrich Chemical Co., Milwaukee, Wis. Fe(III) tetraphenylporphyrin derivates were either purchased from Midcentury Chemicals or synthesized by pyrrole-benzaldehyde condensation in a propionic acid reflux, by the method of A. D. Adler, F. R. Longo, J. D. Finarelli, J. Goldmacher, J. Assour, and L. Korsakoff, *J. Org. Chem.*, 32, 476 (1967). Iron was inserted using $FeCl_2$ in dimethylformamide, as taught by A. D. Adler, F. R. Longo, and V. Varadi, *Inorg. Syn.*, 16, 213–220 (1976).

General synthetic references are Dolphin, D. Ed., "The Porphyrins", Vol. 6, Chap 3–20, pp. 290-339 (Academic Press: New York, 1979); Morgan, B., Dolphin, D. *Struct. Bonding* (Berlin), 64 (Met. Complexes Tetrapyrrole Ligands I), pp. 115-203 (1987); Smith, Kevin M.; Cavaleiro, Jose A. S. Heterocycles, 16(7), 1947-63 (1987).

Still other synthetic techniques include the methods of Lindsey, et al., *J. Org. Chem.* 52, 827-836 (1987); Momenteau, M.; Loock, B.; Huel, C.; Lhoste, J. M. *J. Chem. Soc., Perkin Trans. I*, 283 (1988); Morgan, B.; Dolphin, D. *J. Org. Chem.* 52, 5364-5374 (1876); Smith, K. M.; Parish, D. W.; Inouye, W. S. *J. Org. Chem.* 51, 666-671 (1986); and Smith, K. M.; Minnetian, O. M. *J. Chem. Soc., Perkin Trans. I*, 277-280 (1986). Other references to metal insertion include Buchler, J. E., "The Porphyrins", vol. 1, ch. 10, Dolphin, D., ed. (Academic Press, New York 1979); Lavallee, D. K. *Coord. Chem. Rev.* 61, 55–96 (1985); Lavallee, D. K. *Comments Inorg. Chem.* 5, 155-174 (1986).

Phthalocyanines can be synthesized by the condensation of phthalonitrile and its derivatives. Functionalization of the phthalocyanine ring system is readily achieved, using the method of Langlois, et al., "Biological activities of phthalocyanines—IV. Type II sensitized photoxidation of L-tryptophan and cholesterol by sulfonated metallo phthalocyanines." *Photochem. Photobiol,.* 44, 117–123, (1986), and Spikes, J. D. *Photochem. Photobiol.*, 43, 691-699, (1986).

Porphyrins and phthalocyanines may also be obtained from commercial sources including Aldrich Chemical Co., Milwaukee, Wis., Porphyrin Products, Logan, Utah, and Midcentury Chemicals, Posen, Ill.

Chlorins, another group of useful porphyrins, can be made using the method described by Oseroff, et al., *Proc. Natl. Acad. Sci.* USA, 83, 8744-8748 (1986).

One can screen the porphyrins for inhibition of HIV using various experimental techniques. One technique involves the inhibition of viral replication in human peripheral blood mononuclear (PBM) cells. The amount of virus produced is determined by measuring the quantity of virus-coded reverse transcriptase (an enzyme found in retroviruses) which is present in the culture medium. Another technique involves measuring inhibition of purified reverse transcriptase activity in a cell free system. Examples of methods for screening which are known to those skilled in the art are described in more detail as follows.

Methodology for Testing Antiviral Drugs for Inhibition or Replication of HIV-1 in Human Peripheral Blood Mononuclear (PBM) Cells HIV-1 and B virus seronegative donors are isolated by Ficoll-Hypaque discontinuous gradient centrifugation at $1,000 \times g$ for 30 minutes, washed twice in PBS and pelleted at $300 \times g$ for 10 minutes. Before infection, the cells are stimulated by phytohemagglutinin (PHA) at a concentration of 16.7 µg/ml for three days in RPMI 1640 medium supplemented with 15% heat-inactivated fetal calf serum, 1.5 mM L-glutamine, penicillin (100 U/ml), streptomycin (100 µg/ml), and 4 mM sodium bicarbonate buffer.

HIV-1 (strain LAV-1) is obtained from the Center for Disease Control, Atlanta, and propagated in PHA-stimulated human PBM cells using RPMI 1640 medium as above without PHA and supplemented with 7% interleuken-2 (Advanced Biotechnologies, Silver Spring, Md.), 7 µg/ml DEAE-dextran (Pharmacia, Uppsala, Sweden), and 370 U/ml anti-human leukocyte (alpha) interferon (ICN, Lisle, Ill.). Virus is obtained from cell-free culture supernatant and stored in aliquots at $-70°$ C. until used.

Addition of compounds. Uninfected PHA-stimulated human PBM cells are uniformly distributed among 25 $cm^3$ flasks to give a 5 ml suspension containing about $1 \times 10^6$ cells/ml. Suitable dilutions of HIV are added to infect the cultures. The mean reverse transcriptase (RT) activity of the inocula is 50,000 dpm/ml which was equivalent to about 100 $TCID_{50}$, determined as described in *AIDS Res. Human Retro.* 3,71-85 (1987). The porphyrin compounds, at twice their final concentrations in 5 ml of RPMI 1640 medium, supplemented as described above, are added to the cultures. Uninfected and untreated PBM cells are grown in parallel as controls. The cultures are maintained in a humidified 5% $CO_2$—95% air incubator at 37° C. for five days after infection at which point all cultures are sampled for supernatant RT activity. Preliminary studies indicated that the maximum RT levels were obtained at that time.

The RT assay is performed by a modification of the method of Spira, et al, in *J.Clin.Microbiol.* 25,97-99 (1987) in 6-well microtiter plates. The radioactive cocktail (180 $\mu$l) containing 50 mM Tris-Hcl pH 7.8, 9 mM $MgCl_2$, 5 mM dithiothreitol 4.7 $\mu$g/ml $(rA)_n \cdot (dT)_{12-18}$, 140 $\mu$M dATP and 0.22 $\mu$M[$^3$H]dTTP (specific activity 78.0 Ci/mmol, equivalent to 17,300 cpm/pmol; NEN Research Products, Boston, Mass.) is added to each well. The sample (20 $\mu$l) is added to the reaction mixture and incubated at 37° C. for two hours. The reaction is terminated by the addition of 100 $\mu$l 10% trichloroacetic acid (TCA) containing 0.45 mM sodium pyrophosphate.

The acid insoluble nucleic acid which precipitated is collected on glass filters using a Skatron semi-automatic harvester. The filters are washed with 5% TCA and 70% ethanol, dried, and placed in scintillation vials. Four ml of scintillation fluid (Econofluor, NEN Research Products, Boston Mass.) is added and the amount of radioactivity in each sample determined using a Packard Tri-Carb liquid scintillation analyzer (model 2,000CA). The results are expressed in dpm/ml of original clarified supernatant.

Methodology for Testing Antiviral Drugs for Toxicity and Inhibition of Cell proliferation The compounds are evaluated for their potential toxic effects on uninfected PHA-stimulated human PBM cells. Flasks are seeded so that the final cell concentration is $3 \times 10^5$ cells/ml. The cells are cultured with and without the test compound for 6 days at which time aliquots are counted for cell viability.

Methodology for Testing Antiviral Drugs for Inhibition of HIV-1 Reverse Transcriptase Cells and viruses are as described above. Reverse transcriptase is purified from detergent disrupted HIV-1 infected cells using DEAE and phosphocellulose column chromatography, according to the method of Abrell and Gallo, *J. Virol.* 12,431-439 (1973). Cocktail, template, compound to be tested and reverse transcriptase are mixed together on ice, then incubated for one hour at 37° C. The DNA synthesized is acid precipitated and the radioactivity measured, as described by Eriksson, B., et al., *Antimicrobial Agents and Chemotherapy* 31, 600-604 (1977).

Methodology for Testing Antiviral Drugs for Inhibition of Replication of HSV-1 and HSV-2

Compounds are tested for Inhibition of herpes simplex virus type 1 and herpes simplex virus type 2 using the method of Schinazi, et al., *Antimicrobial Agents and Chemotherapy* 22, 499-507 (1982). This is a plaque assay using Vero cells (African green monkey cells) infected with HSV.

Examples of Compounds Having Antiviral Activity and Low Toxicity $EC_{50}$ the median effective concentration of the compound as determined from inhibition of HIV replication in PBM cells. The therapeutic index of a compound is determined by dividing the inhibitory or lethal dose for 50% of the population ($IC_{50}$ or $LD_{50}$) by the effective dose for 50% of the population ($EC_{50}$).

A variety of porphyrins and phthalocyanines were tested for anti-HIV activity. Inhibition of replication of virus in cell culture is shown in Table I. Inhibition of reverse transcriptase is described in Table II. None of these compounds were toxic at concentrations of 1 $\mu$M, 10 $\mu$M and 100 $\mu$M as determined by trypan blue exclusion by uninfected human PBM cells. As a result, all of the compounds active at less than 10 $\mu$M have very favorable therapeutic indices.

A variety of porphyrins were also tested for inhibition of herpes simplex type 1 and type 2 (HSV-1 and HSV-2) activity. The results are described in Table III. With few exceptions, no significant inhibition of HSV-1 or HSV-2 was noted. Similar results were obtained with Coxsackievirus strain B4.

The results demonstrate that the non-metalloporphyrins are generally more active than the metalloporphyrins. However, porphyrin derivatives containing iron were the least active of the metalloporphyrins. Copper and nickel substituted porphyrins and phthalocyanines were significantly more active. Porphyrins having a positive charge, negative charge, and neutral charge, under physiological conditions, were also tested and examples found to have HIV inhibitory activity. As a general rule, the positively charged porphyrins are more active under the assay conditions.

To insure that light is not required for antiviral activity, compounds were tested for inhibition of HIV, HSV-1 and HSV-2 replication in cell culture both in the dark and in the light. No significant differences in activity in inhibition of HIV by 5,10-Diphenyl-15,20-di(N-methyl-4-pyridyl)-porphyrin Cl-, nor of HSV-1 or HSV-2 by any of several compounds, were observed.

TABLE I

| Inhibition of HIV Replication in PBM Cells | |
|---|---|
| Compound Name (Code) | $EC_{50}$ ($\mu$M) |
| Natural Porphyrins | |
| Protoporphyrin, disodium salt (PPIX) | 3.62, 0.48 |
| Protoporphyrin IX dimethyl ester (PPIXDME) | 1.01, >10 |
| Synthetic Porphyrins | |
| 5,10-Diphenyl-15,20-di (N-methyl-3-pyridyl)-porphyrin Cl—(CP-3) | 2.28 |
| 5,10-Diphenyl-15,20-di (N-methyl-4-pyridyl)-porphyrin Cl—(CP-4) | 0.38, 0.43* |
| 5,15-Diphenyl-10,20-di (N-methyl-4-pyridyl)-Cl-porphyrin Cl—(TP-3) | 0.34, 1.87 |
| 5,15-Diphenyl-10,20-di (N-methyl-3-pyridyl)-porphyrin Cl—(TP-4) | <1, 0.76 |
| Tetra-(N-methyl-4-pyridyl)-porphyrin tosylate salt (TMPyP) | 3.23, 0.66 |
| Meso-tetraphenylporphine (TPP) | 13.7, >10 |
| Tetra-(4-carboxyphenyl)-porphyrin (TPP(4-$CO_2$H)$_4$) | 1.11, 10.7 |
| Tetra-(4-methylphenyl)-porphyrin (TPP(4-Me)$_4$) | 0.754, 10 |
| Tetra-(3-methylphenyl)-porphyrin (TPP(3-Me)$_4$) | 0.05, 10 |
| Tetra-(4-hydroxyphenyl)-porphyrin (TPP(4-OH)$_4$) | 0.6, 0.7 |
| Tetra-(4-chlorophenyl)-porphyrin (TPP(4-Cl)$_4$) | ~100 |
| Natural Metalloporphyrins | |
| Hemin, bovine, (chloro | 49.3 |

TABLE I-continued

Inhibition of HIV Replication in PBM Cells

| Compound Name (Code) | EC$_{50}$ ($\mu$M) |
|---|---|
| protoporphyrin IX Fe(III)) (FePPIXCl) | |
| Synthetic Metalloporphyrins | |
| Fe(III)-tetraphenylporphyrin chloride (FeTPPCl) | ~100 |
| Fe(III)-tetra-(4-methylphenyl)-porphyrin chloride (FeTPP)(4-Cl)$_4$ | >100 |
| Fe(III)-tetra-(N-methyl-4-pyridyl)-porphyrin chloride (FeTMPyP) | 78.1 |
| Fe(III)-mu-oxo-dimer of tetraphenyl-porphyrin ($\mu$-oxo-TPP) | >100 |
| Cu(II)-5,10-diphenyl-15,20-di(N-methyl-4-pyridyl)-porphyrin (Cu—CP4) | 4.76, 5.78 |
| Ni(II)-5,10-diphenyl-15,20-di(N-methyl-4-pyridyl)-porphyrin (Ni—CP4) | 3.44, 6.54 |
| Phthalocyanines | |
| Copper phthalocyanine tetrasulfonic acid tetrasodium salt (CuPHTHS$_4$) | 22.4 |
| Nickel phthalocyanine tetrasulfonic acid (NiPHTHS$_4$) | 1.06 |
| Copper phthalocyanine 3,4' 4'',4'''-tetrasulfonic acid (CuPHTHS$_4$)(3,4,4,4) | ≦1 |
| Copper phthalocyanine (CuPHTH) | 46.9 |
| Copper-4,4',4'',4'''-tetra-aza-29H, 31H-phthalocyanine (CuPHTHN$_4$) | 100 |
| Cobalt phthalocyanine (CoPHTH) | 100 |
| Reactive Blue 15 | <1 |
| Silicon phthalocyanine dichloride (SiPHTHCl$_2$) | <1 |

*Tested in darkness

TABLE II

Inhibition of HIV Reverse Transcriptase

| Compound (Code) | EC$_{50}$ ($\mu$M) |
|---|---|
| Natural Porphyrins | |
| Protoporphyrin, disodium salt (PPIX) | >100 |
| Protoporphyrin IX dimethyl ester (PPIXDME) | >100 |
| Synthetic Porphyrins | |
| 5,10-Diphenyl-15,20-di(N-methyl-3-pyridyl)-porphyrin Cl—(CP-3) | 41.6 |
| 5,10-Diphenyl-15,20-di(N-methyl-4-pyridyl)-porphyrin Cl—(CP-4) | 26.9 |
| 5,15-Diphenyl-10,20-di(N-methyl-4-pyridyl)-porphyrin Cl—(TP-3) | 7.3 |
| 5,15-Diphenyl-10,20-di(N-methyl-3-pyridyl)-porphyrin Cl—(TP-4) | 6.9 |
| Meso-tetraphenylporphine (TPP) | >100 |
| Tetra-(4-carboxyphenyl)-porphyrin (TPP(4-CO$_2$H)$_4$) | 1.1 |
| Tetra-(4-methylphenyl)-porphyrin (TPP(4-Me)$_4$) | >100 |
| Natural Metalloporphyrins | |
| Hemin, (chloroprotoporphyrin IX Fe(III)) (FePPIXCl) | 20.5 |
| Synthetic Metalloporphyrins | |
| Cu(II)-5,10-diphenyl-15,20-di(N-methyl-4-pyridyl)-porphyrin (Cu—CP4) | 57.4 |
| Ni(II)-5,10-diphenyl-15,20-di(N-methyl-4-pyridyl)- | 24.8 |

TABLE II-continued

Inhibition of HIV Reverse Transcriptase

| Compound (Code) | EC$_{50}$ ($\mu$M) |
|---|---|
| porphyrin (Ni—CP4) | |

TABLE III

Inhibition of HSV Type 1 and HSV Type 2

| | EC$_{50}$ ($\mu$M) | | | |
|---|---|---|---|---|
| | HSV type 1 | | HSV type 2 | |
| Compound (Code) | Light | Dark | Light | Dark |
| Natural Porphyrins | | | | |
| Protoporphyrin, disodium salt (PPIX) | <0.01 | | 0.05 | 10 |
| Tetra-(N-methyl-4-pyridyl)-porphyrin tosylate salt (TMPyP) | 0.03 | 0.04 | >1 | >10 |
| Meso-tetraphenyl-porphine (TPP) | 10 | >10 | >10 | >10 |
| Protoporphyrin IX dimethyl ester (PPIXDME) | 10 | >10 | >10 | >10 |
| Tetra-(4-carboxy-phenyl-porphyrin (TPP(4-)CO$_2$H)$_4$) | 10 | 2.5 | >10 | >10 |
| Tetra-(4-methyl-phenyl)-porphyrin (TPP(4-Me)$_4$) | 1 | >10 | >10 | 3.95 |
| Tetra-(3-methyl-phenyl)-porphyrin (TPP(3-Me)$_4$) | >10 | >10 | >10 | |
| Tetra-(4-hydroxy-phenyl-)porphyrin (TPP(4-OH)$_4$) | >10 | >10 | >10 | >10 |

The compositions can be used for the in vitro inhibition of HIV replication, for example, in blood obtained for transfusion purposes or in sterilization of pharmaceuticals derived from blood. Although light does not appear to be required, it may enhance anti-HIV activity in some cases.

Humans suffering from infections caused by HIV can be treated by administering to the patient a pharmaceutically effective amount of the above described compounds in the presence of a pharmaceutically acceptable carrier or diluent to produce an effective concentration. Some porphyrins are water soluble and may be administered in sterile water or physiological saline or phosphate buffered saline (PBS). Many porphyrin-like compounds are not water soluble and are preferably administered in pharmaceutically acceptable non-aqueous carriers including oils and liposomes. Solubility of the porphyrins can be increased by techniques known to those skilled in the art including introducing hydroxyl groups and changing the counter ions.

The compounds according to the present invention are included in the pharmaceutically acceptable carrier or diluent in an amount sufficient to exert a therapeutically useful inhibitory effect on HIV in vivo without exhibiting adverse toxic effects on the patient treated. By "HIV inhibitory amount" is meant an amount of active ingredient sufficient to exert an HIV inhibitory effect as measured by, for example, an assay such as the ones described herein.

There may also be included as part of the composition pharmaceutically compatible binding agents, and/or adjuvant materials. The active materials can also be mixed with other active materials including antibiotics, antifungals, other antivirals and immunostimulants which do not impair the desired action and/or supplement the desired action. The active materials according to the present invention can be administered by any route, for example, orally, parenterally, intravenously, intradermally, subcutaneously, or topically, in liquid or solid form.

A preferred mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methylparabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

These preparations should produce a serum concentration of active ingredient of from about 0.2 to 40 $\mu$M. A preferred concentration range is from 0.2 to 20 $\mu$M and most preferably about 1 to 10 $\mu$M. However, the concentration of active ingredient in the drug composition itself will depend on bioavailability of the drug and other factors known to those of skill in the art.

It is to be noted that dosage values will also vary with the specific severity of the disease condition to be alleviated, and that, for any particular subject, specific dosage regimens should be adjusted to the individual need and the professional judgment of the person administering or supervising the administration of the aforesaid compositions. The concentration ranges set forth herein are exemplary only and not intended to limit the scope or practice of the invention. The active ingredient may be administered at once, or may be divided into a number of smaller doses to be administered at varying intervals of time.

The compositions of the present invention are prepared as formulations with pharmaceutically acceptable carriers. Preferred are those carriers that will protect the active compound against rapid elimination from the body, such as a controlled release formulation, including implants and microencapsulated delivery systems. Biodegradable, biocompatible polymers can be used, such as polyanhydrides, polyglycolic acid, collagen, and polylactic acid. Methods for preparation of such formulations will be apparent to those skilled in the art.

Liposomal suspensions (including liposomes targeted to infected cells with monoclonal antibodies to viral antigens) are also preferred as pharmaceutically acceptable carriers. Methods for encapsulation or incorporation of porphyrins into liposomes are described by Cozzani, I.; Jori, G.; Bertoloni, G.; Milanesi, C.; Sicuro, T. *Chem. Biol. Interact.* 53, 131-143 (1985) and by Jori, G.; Tomio, L.; Reddi, E.; Rossi, E. *Br. J. Cancer* 48, 307-309 (1983). These may also be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Other methods for encapsulating porphyrins within liposomes and targeting areas of the body are described by Sicuro, T.; Scarcelli, V.; Vigna, M. F.; Cozzani, I. *Med. Biol. Environ.* 15(1), 67-70 (1987) and Jori, G.; Reddi, E.; Cozzani, I.; Tomio, L. *Br. J. Cancer,* 53(5), 615-21 (1986).

Modifications and variations of the present invention, compositions containing porphyrins or porphyrin-like compounds, such as phthalocyanines, and methods for using the compositions, will be obvious to those skilled in the art from the foregoing detailed description of the invention. Such modifications and variations are intended to come within the scope of the appended claims.

We claim.

1. A method for inhibiting infection or replication of human immunodeficiency virus comprising administering an effective amount of a porphyrin, porphyrin-like compound or a derivative thereof to inhibit HIV infection in cells in combination with a carrier suitable for administration of porphyrin to cells in vitro.

2. The method of claim 1 wherein the porphyrin, porphyrin-like compound or derivative is selected from the group consisting of porphyrins isolated from nature, synthetic porphyrins, phthalocyanines, chlorins, substituted porphyrins or porphyrin-like compounds having one or more symmetrically or unsymmetrically located substituents on any of the positions of the ring periphery, neutrally charged porphyrins, positively charged porphyrins, negatively charged porphyrins, charged porphyrins in combination with counterions, porphyrins or porphyrin-like compounds covalently attached to other molecules, porphyrins or porphyrin-like compounds where conjugation of the ring is altered by addition of one or more substituents, metalloporphyrins, metallophthalocyanines, and metallochlorins.

3. The method of claim 2 wherein the compound is selected from the group consisting of 5,10-Diphenyl-15,20-di(N-methyl-3-pyridyl)-porphyrin; 5,10-Diphenyl-15,20-di(N-methyl-4-pyridyl)-porphyrin; metallo-derivatives of 5,10-Diphenyl-15,20-di(N-methyl-4-pyridyl)-porphyrin; 5,15-Diphenyl-10,20-di(N-methyl-3-pyridyl)-porphyrin; Protoporphyrin; Tetra-(N-methyl-4-pyridyl)-porphyrin; Meso-tetraphenylporphine; Protoporphyrin IX dimethyl ester; Tetra-(4-carboxyphenyl)-porphyrin; Tetra-(4-methylphenyl)-porphyrin; Tetra-(3-methylphenyl)-porphyrin; Tetra-(4-hydroxyphenyl)-porphyrin, Copper phthalocyanine tetrasulfonic acid tetrasodium salt, Nickel phthalocyanine tetrasulfonic acid, Copper phthalocyanine 3,4',4'',4'''-tetrasulfonic acid, Copper phthalocyanine, Reactive Blue 15, Silicon phthalocyanine dichloride, and salts thereof.

4. The method of claim 1 wherein the material is blood and said compound is administered in a pharmaceutically effective dosage to inhibit viral replication in vivo.

5. The method of claim 4 wherein said compound is administered to produce a blood serum concentration of between approximately 0.2 to 40 $\mu$M.

6. The method of claim 5 wherein said compound is administered to produce a blood serum concentration of between approximately 0.2 to 20 $\mu$M and most preferably about 1 to 10 $\mu$M.

7. The method of claim 1 further comprising providing a pharmaceutically acceptable carrier in combination with the compound.

8. The method of claim 7 wherein the pharmaceutically acceptable carrier is suitable for injection.

9. The method of claim 7 wherein said carrier is a liposomal suspension.

10. The method of claim 7 comprising encapsulating the compound with a pharmaceutically acceptable carrier in an enteric coating.

11. The method of claim 7 further comprising encapsulating the compound in a biodegradable implant.

12. The method of claim 1 further comprising administering a therapeutically effective amount of at least one compound selected from the group consisting of antibiotics, antivirals, antifungals, and immunostimulants.

13. The method of claim 12 wherein the antiviral is selected from the group consisting of HPA-23, interferons, ribavirin, phosphonoformate, ansamycin, suramin, imuthiol, penicillamine, carbovir, 3'-azido-3'-deoxythymidine, 2',3'-dideoxycytidine, 2',3'-dideoxyinosine, 2',3'-dideoxyadenosine, 3'-azido-2',3'-dideoxyuridine, 2',3'-dideoxy-2',3'-didehydrocytidine, 3'-deoxy-2',3'-didehydrothymidine and 3'-azido-5-ethyl-2',3'-dideoxyuridine.

* * * * *